United States Patent [19]
Moenning

[11] Patent Number: 6,063,060
[45] Date of Patent: May 16, 2000

[54] MINIMALLY INVASIVE MEDICAL APPARATUS FOR DISPENSING A BIOLOGICALLY ACTIVE COMPOUND AND AN ASSOCIATED MEDICAL PROCEDURE FOR DISPENSING A BIOLOGICALLY ACTIVE COMPOUND

[76] Inventor: Stephen P. Moenning, 1940 Jamaica Way, Punta Gorda, Fla. 33950

[21] Appl. No.: 09/097,325

[22] Filed: Jun. 15, 1998

[51] Int. Cl.⁷ .................................................. A61M 5/178
[52] U.S. Cl. ........................ 604/164; 604/171; 604/264
[58] Field of Search .................................. 604/890.1, 27, 604/30, 32, 164, 169, 171–173, 264

[56] References Cited

U.S. PATENT DOCUMENTS

| | | | |
|---|---|---|---|
| 4,540,411 | 9/1985 | Bodicky | 604/169 |
| 5,013,296 | 5/1991 | Buckberg et al. | 604/44 |
| 5,250,038 | 10/1993 | Melker et al. | 604/264 |
| 5,533,896 | 7/1996 | Mottola et al. | 604/264 |
| 5,843,017 | 12/1998 | Yoon | 604/22 |

*Primary Examiner*—Wynn Wood Coggins
*Assistant Examiner*—Deborah Blyveis
*Attorney, Agent, or Firm*—Maginot, Addison & Moore

[57] ABSTRACT

A medical apparatus includes a trocar assembly including a cannula and a trocar, wherein (1) the cannula has a working channel defined therein through which medical instruments may be advanced, (2) the cannula includes a fluid delivery channel which is distinct from the working channel, and (3) the fluid delivery channel has an exit port. The medical apparatus also includes a chemical container having an interior void defined therein for receiving the biologically active compound. The interior void of the chemical container is in fluid communication with the exit port through the fluid delivery channel, whereby the biologically active compound may be delivered through the fluid delivery channel to an outer surface of the cannula. An associated medical procedure for dispensing a biologically active compound is also disclosed.

10 Claims, 8 Drawing Sheets

MINIMALLY INVASIVE MEDICAL APPARATUS FOR DISPENSING A BIOLOGICALLY ACTIVE COMPOUND AND AN ASSOCIATED MEDICAL PROCEDURE FOR DISPENSING A BIOLOGICALLY ACTIVE COMPOUND

BACKGROUND OF THE INVENTION

The present invention generally relates to a medical apparatus and procedure for dispensing a biologically active compound. The present invention particularly relates to a medical apparatus and procedure for dispensing a biologically active compound during a minimally invasive surgical technique, such as laparoscopic surgery.

Minimally invasive surgical techniques, such as laparoscopic surgery, typically include the use of a trocar assembly. A trocar assembly includes a trocar (sometimes referred to as an "obturator") positioned within the lumen of a cannula. The trocar and cannula are advanced through a body cavity wall so as to create a small opening or a port site wound therein. The trocar is then completely removed from the lumen of the cannula such that the cannula's lumen provides an entrance for laparoscopic instruments into the interior of the body cavity. The body cavity is then insufflated with an inert gas, such as $CO_2$, to provide easier access to the organs contained therein. An alternative to insufflation, which also aids in intra-abdominal visualization and provides access to the organs, is a mechanical lifting device. Once the surgery is complete the cannula is completely removed from the port site wound to rapidly desufflate the body cavity.

Surgery performed by using minimally invasive techniques is generally associated with lower postoperative morbidity, slower tumor growth, shorter postoperative stay, less postoperative pain, decreased cost, and quicker recovery as compared to "open" or conventional surgical techniques[1,2,3,4,5,6]. Because of the aforementioned advantages, these minimally invasive techniques are being applied to an increasing variety of all surgical procedures. For example, laparoscopic procedures for the resection of malignancies have emerged. In particular, laparoscopic colectomy for carcinoma of the colon has been developed, and it has been reported that the initial results of these procedures have advantages over operations performed in the traditional open manner[5,6,14]. Moreover, it is hoped that the long term results of these procedures will be comparable, or better than, those performed in the traditional open manner.

However, the development of laparoscopic surgery for cancer has been hindered because of the major concern regarding the implantation of tumor cells in the port site wound[2,3,6,7]. In fact, numerous port site recurrences have been documented in the medical literature heretofore, and these recurrences are associated with a decreased survival rate for patients who may have had a curative cancer[2,3,6,7]. Specifically, the medical literature reports that the incidence of tumor cell implantation ranges from as high as 20% to as low as 0%[8]. The studies generating the aforementioned data utilized highly skilled and experienced laparoscopic surgeons practicing at major university programs. However, in spite of utilizing highly skilled and experienced laparoscopic surgeons, the data indicates that the incidence of tumor cell implantation in the surgical wound is greater when employing laparoscopic techniques as compared to when conventional surgical techniques are used (i.e. 0.6% implantation incidence for conventional techniques[9] compared to 1% incidence for laparoscopic techniques[10]).

Several mechanisms may be responsible for the above discussed implantation of tumor cells in the port site wound. For example, minimally invasive surgical techniques for treating cancer require the insertion and removal of laparoscopic instruments or cameras through the lumen of the cannula. In addition, these surgical techniques require that the cannula itself be moved relative to the port site wound such that the cannula is advanced further into, or withdrawn from, the body cavity[11]. Moving the cannula in the above described manner facilitates a surgeon's ability to optimally locate instruments within the body cavity thereby helping to ensure the successful completion of the medical procedure. However, the aforementioned manipulations of the laparoscopic instruments and cannula may result in the exposure of the port site wound to exfoliated cancer cells which creates a risk of implanting tumor cells in the walls of the port site wound[11,12]. In particular, exfoliated cancer cells may adhere to and thus contaminate a portion of the exterior surface of the cannula[11,12]. The contaminated portion of the exterior surface of the cannula may then be advanced into contact with the port site wound during insertion and removal from the port site wound[11,12]. This contact may dislodge the exfoliated cancer cells from the exterior surface of the cannula and thus cause the exfoliated cancer cells to be implanted in the port site wound[11,12].

Furthermore, studies have shown that a physician may undergo a significant learning curve before becoming proficient in the performance of advanced laparoscopic surgery, such as cancer surgery[3,13,16]. As a result, a relatively inexperienced surgeon may have a tendency to manipulate or handle a tumor to a greater degree during a surgical procedure than an experienced surgeon. Studies have shown a 14.6% incidence of viable tumor cells in proximity of the specimen where the surgeon is working with his or her instruments[15]. In addition, an inexperienced surgeon may have a tendency to insert and withdraw an instrument through the lumen of the cannula a greater number of times than an experienced surgeon. The above described increased manipulation of the instrument or the tumor can result in a greater incidence of tumor cell implantation in the port site wound[11,12].

Regardless of how these cells contaminate the wound, once implanted therein, viable tumor cells can cause a subcutaneous metastases or "port site recurrence" after the resection of malignant tissue. These "port site recurrences" have delayed the advancement of laparoscopic cancer surgery[2,6,7,8,9,10,11,12] into all fields of cancer surgery, and is one reason why the benefits of laparoscopic surgery have not been available to cancer patients.

Furthermore, laparoscopic surgery performed for general surgery, gynecological surgery, urological surgery, or any other intra-abdominal infection is associated with a small but real incidence of port site wound infection[1]. The infecting bacteria causing these illnesses can contaminate the port site wound in the same manner as discussed above with regard to tumor cell contamination, and these infections can increase a patient's morbidity and consequently the length of a patient's hospital stay, thereby considerably increasing their hospital bill.

One way of addressing the problem of potential tumor or infectious cell implantation in the port site wound is to apply a biologically active compound, such as a cytotoxic agent which kills tumor or infectious cells, on a medical apparatus (e.g. a trocar assembly) utilized in the laparoscopic procedure. By placing such a compound on the medical apparatus the biologically active compound becomes disposed on the interior surface of the body cavity and on the surface of the port site wound. Having the biologically active compound disposed on the medical apparatus, the interior surface of the body cavity, and the surface of the port site wound establishes a "pharmacological barrier" which prevents any viable tumor or infectious cells from becoming implanted in the port site wound.

Heretofore, biologically active compounds were disposed on the medical apparatus by various methods. For example, dipping the medical apparatus in a solution or suspension of the biologically active compound, applying the biologically active compound to the medical apparatus with an applicator such as a cotton swab, or injecting the intraperitoneal surface with the biologically active compound[16,17]. However, the aforementioned methods of administering the biologically active compound suffer from several drawbacks. For example, these methods are inconvenient, messy, inexact, or highly variable. In addition, these methods do not allow the amount of the biologically active compound administered to the patient via the medical apparatus to be appropriately controlled. Controlling the amount administered to a patient is important since it allows the physician to carefully adjust the dose of the biologically active compound and thus avoid any undesirable side effects while maximizing the delivery of the biologically active compound. In addition, controlling the dose allows the physician to collect dose response data, and thus measure the effectiveness of various pharmacological regimens. With the recent advances in the fields of biotechnology, genetic engineering, and pharmacology, there is a need to accurately, efficiently, and reproducibly deliver current and future biologically active agents during the performance of a minimally invasive surgical technique.

What is needed therefore is a medical apparatus and procedure for disposing a biologically active compound which addresses the above described drawbacks.

TABLE OF REFERENCES CITED IN THE BACKGROUND

1. Lord et al., *Dis. Col. Rect.* 39(2):148 (1996)
2. Berman, *Important Advances in Oncology* 1996, *Laparoscopic Resection for Colon Cancer: Cause for Pause,* Vincent DeVita Ed., p. 231
3. Falk et al., *Dis. Col. Rect.* 36:28 (1993)
4. Liberman et al., *Surg. Endo.* 10:15 (1996)
5. Whelan et al., *Dis. Col. Rect.* 41(5):564 (1998)
6. Wexner et al., *Am. Surg.* 64(1):12–18 (1998)
7. Greene, *Semin. Lap. Surg.* 2(3):153 (1995)
8. Kazemier, *Surg. Endo.* 9:216 (1995)
9. Reilly et al., *Dis. Col. Rect.* 39(2):200 (1996)
10. Jacquet et al., *Dis. Col. Rect.* 38(10):140 (1995)
11. Reymond et al., *Surg. Endo.* 11:902 (1997)
12. Allardyce et al., *Dis. Col. Rect.* 40(8):939 (1997)
13. Caushaj et al., *Dis. Col. Rect.* 37(4):21 (Podium Abstract 1994)
14. Lee et al., (oral presentation, 6$^{th}$ World Congress of Endoscopic Surgery, June 1998) *Surgical Endoscopy* 12 (5):14 (1998)
15. Russell et al., *Dis. Col. Rect.* 40 (11):1294 (1997)
16. Neuhaus S J, (oral presentation, 6$^{th}$ World Congress of Endoscopic Surgery, June 1998) *Surgical Endoscopy* 12 (5): 515 (1998)
17. Schneider C, (oral presentation, 6$^{th}$ Word Congress of Endoscopic Surgery, June 1998) *Surgical Endoscopy* 12 (5): 517 (1998)

SUMMARY OF THE INVENTION

In accordance with one embodiment of the present invention, there is provided a medical apparatus for dispensing a biologically active compound. The medical apparatus includes a trocar assembly including a cannula and a trocar, wherein (1) the cannula has a working channel defined therein through which medical instruments may be advanced, (2) the cannula includes a fluid delivery channel which is distinct from the working channel, and (3) the fluid delivery channel has an exit port. The medical apparatus also includes a chemical container having an interior void defined therein for receiving the biologically active compound. The interior void of the chemical container is in fluid communication with the exit port through the fluid delivery channel, whereby the biologically active compound may be delivered through the fluid delivery channel to an outer surface of the cannula.

Pursuant to another embodiment of the present invention, there is provided a medical procedure which includes the following steps: (i) creating an opening in a wall of a body cavity, (ii) advancing a medical apparatus through the opening and into the body cavity, the medical apparatus including a trocar assembly having (1) a cannula and a trocar, wherein (A) the cannula has a working channel defined therein through which medical instruments may be advanced, (B) the cannula includes a fluid delivery channel which is distinct from the working channel, and (C) the fluid delivery channel has an exit port, and (2) a chemical container having an interior void defined therein for receiving the biologically active compound, the interior void being in fluid communication with the exit port through the fluid delivery channel, and (iii) advancing the biologically active compound from the interior void of the chemical container onto an exterior surface of the cannula through a fluid path defined by the fluid delivery channel.

According to yet another embodiment of the present invention, there is provided a medical apparatus for dispensing a biologically active compound. The medical apparatus includes a sleeve, wherein (1) the sleeve has a working channel defined therein through which medical instruments may be advanced, (2) the sleeve includes a fluid delivery channel which is distinct from the working channel, (3) the fluid delivery channel has an exit port, and (4) the sleeve includes a housing having an interior cavity defined therein. The medical apparatus also includes a chemical container having an interior void defined therein for receiving the biologically active compound. The interior void of the chemical container is in fluid communication with the exit port through the fluid delivery channel when the chemical container is positioned within the interior cavity of the housing such that the biologically active compound may be delivered through the fluid delivery channel to an outer surface of the sleeve.

It is therefore an object of the present invention to provide a new and useful medical apparatus for protecting a port site wound.

It is another object of the present invention to provide an improved medical apparatus for protecting a port site wound.

It is still another object of the present invention to provide a new and useful medical apparatus for dispensing a biologically active compound.

It is another object of the present invention to provide an improved medical apparatus for dispensing a biologically active compound.

It is moreover an object of the present invention to provide a new and useful medical procedure for protecting a port site wound.

It is still another object of the present invention to provide an improved medical procedure for protecting a port site wound.

It is moreover an object of the present invention to provide a new and useful medical procedure for dispensing a biologically active compound.

It is still another object of the present invention to provide an improved medical procedure for dispensing a biologically active compound.

The above and other objects, features, and advantages of the present invention will become apparent from the following description and attached drawings.

DETAILED DESCRIPTION OF THE PREFERRED EMBODIMENT

Figure 1:
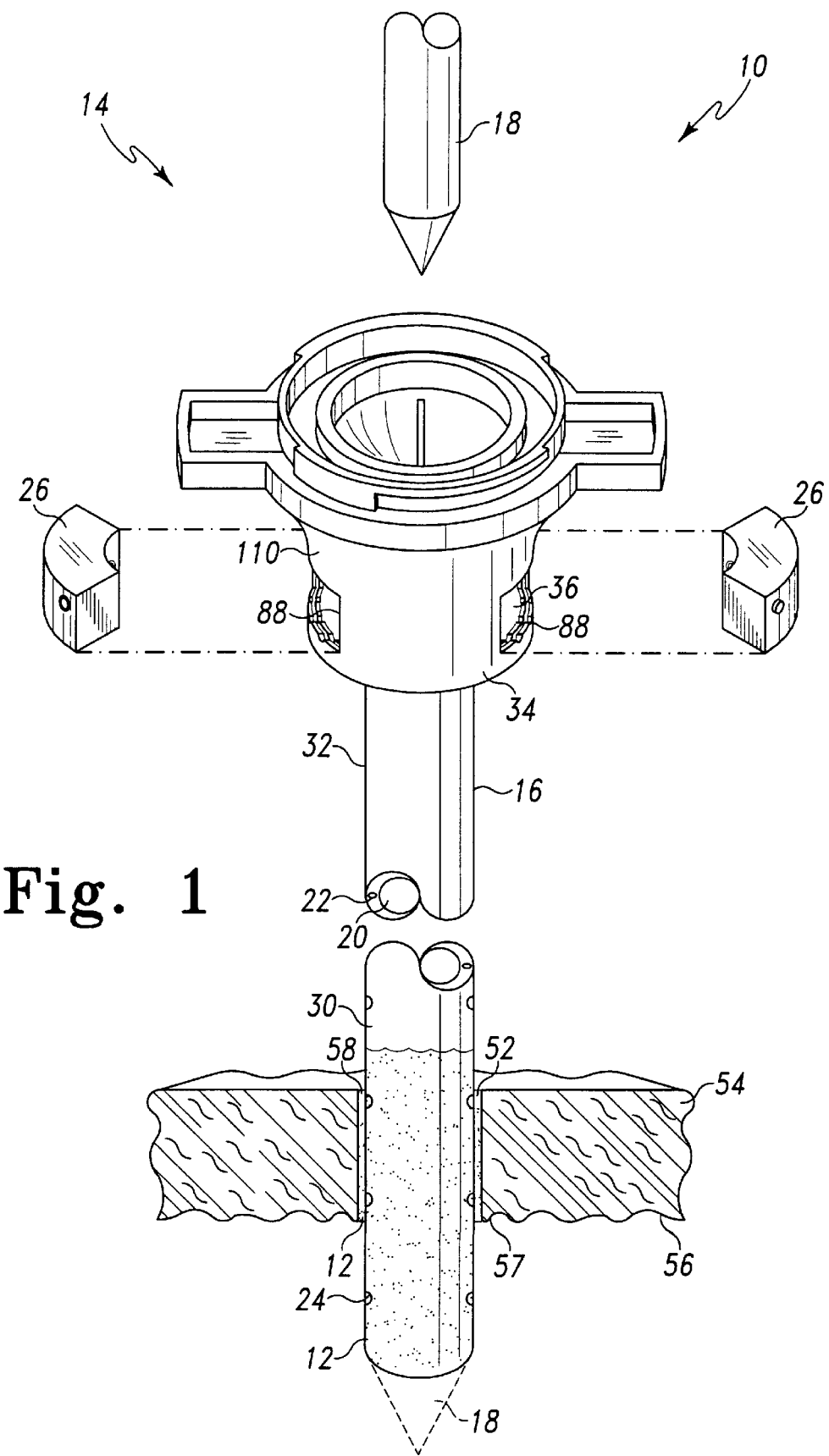
FIG. 1 is an exploded perspective view of a medical apparatus inserted through a body cavity wall which incorporates the features of the present invention therein, with the body cavity wall shown in cross-section for clarity of description.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

First Embodiment of the Invention

Figure 2:
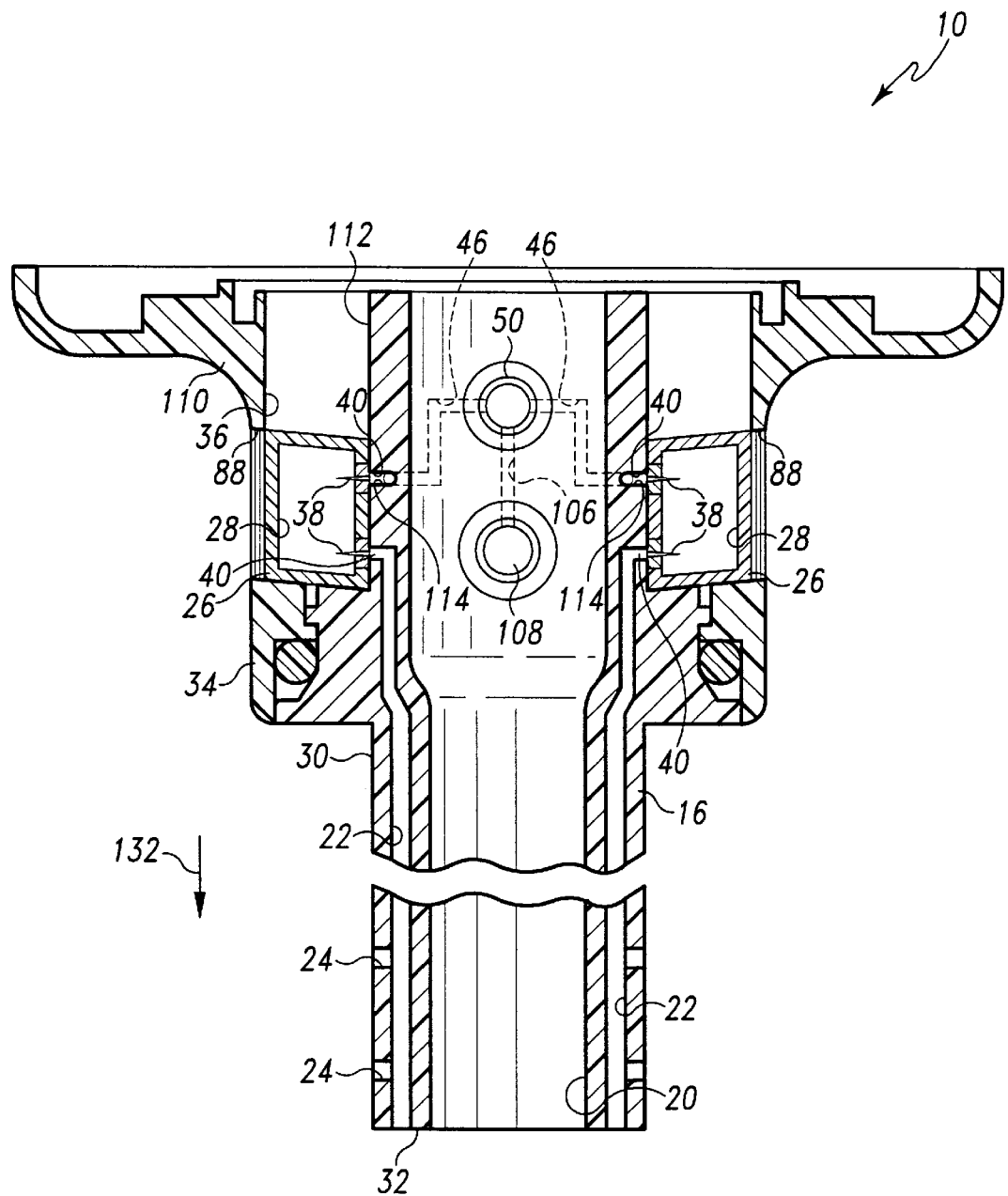
FIG. 2 is an enlarged fragmentary cross sectional view of the medical apparatus of FIG. 1, showing the chemical containers inserted into the housing.
Figure 3:
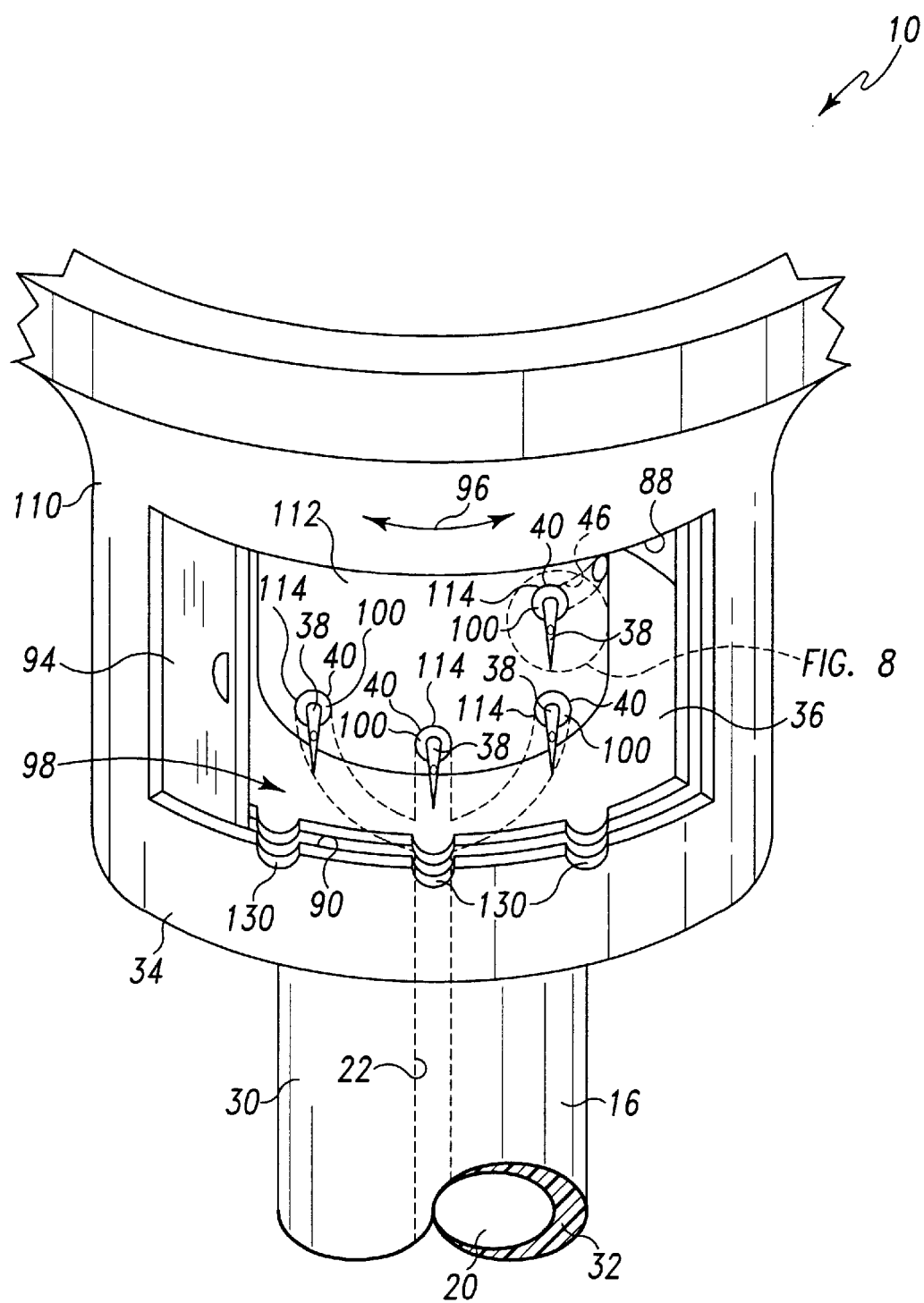
FIG. 3 is an enlarged fragmentary perspective view of the medical apparatus of FIG. 1, showing the interior cavity of the housing.

Referring to FIGS. 1, 2, and 3, there is shown a medical apparatus 10 of the present invention advanced through an opening 52 (i.e. the port site wound) in a wall 54 of a body cavity 56. The medical apparatus 10 includes a trocar assembly 14 and a pair of chemical containers 26. Trocar assembly 14 includes a cannula 16 and a trocar 18. Cannula 16 includes (1) a wall 32 having an outer surface 30, (2) a working channel 20 defined by wall 32, (3) a housing 34, and (4) a pair of fluid delivery channels 22 which are distinct from working channel 20.

Housing 34 includes an exterior wall segment 110 and an interior wall segment 112 (see FIGS. 2 and 3). Housing 34 also includes an annular shaped interior cavity 36 defined between exterior wall segment 110 and an interior wall segment 112. As shown more clearly in FIG. 1, exterior wall segment 110 has a pair of passageways 88 defined therein which lead to interior cavity 36. As shown in FIG. 3, exterior wall segment 110 also has a track 90 defined therein such that one track 90 is positioned within each passageway 88. In addition, each passageway has a door 94 positioned therein such that door 94 is located within track 90. Having the above described arrangement allows each door 94 to slide within track 90 relative to exterior wall segment 110 in the directions indicated by arrow 96. Sliding doors 94 in the aforementioned manner allows each door 94 to be located in an open or a closed position. For example, FIG. 3 shows door 94 in an open position so as to provide access to interior cavity 36 of housing 34.

Figure 6:
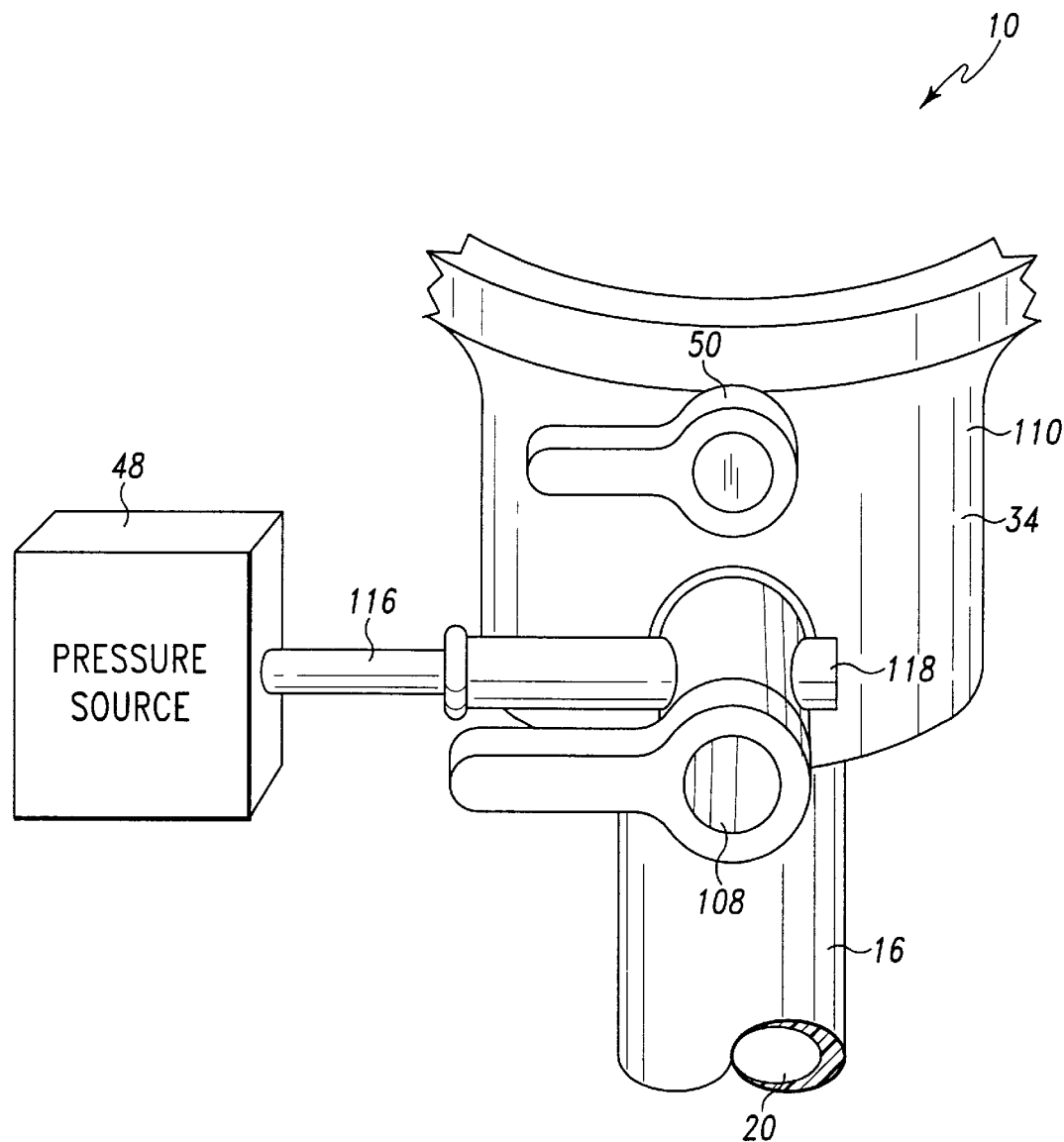
FIG. 6 is a fragmentary perspective view of the medical apparatus of FIG. 1, but with a pressure source schematically shown coupled thereto.

Referring now to FIGS. 2 and 6, housing 34 also has an insufflation valve 108 and a pressure control valve 50 attached thereto. Insufflation valve 108 and pressure control valve 50 extend through exterior wall segment 110 and are attached to interior wall segment 112. Insufflation valve 108 is in fluid communication with working channel 20. As shown in FIG. 2, insufflation valve 108 is also in fluid communication with pressure control valve 50 via a bleed line 106 defined in interior wall segment 112. Pressure control valve 50 is positioned within a pressure line 46 defined in interior wall segment 112. Pressure line 46 has a pair of entrance ports 114 (also see FIGS. 3 and 8) which lead to interior cavity 36 of housing 34. Each entrance port 114 defines an entrance port end wall 40 (also see FIG. 3 and 8).

Figure 8:
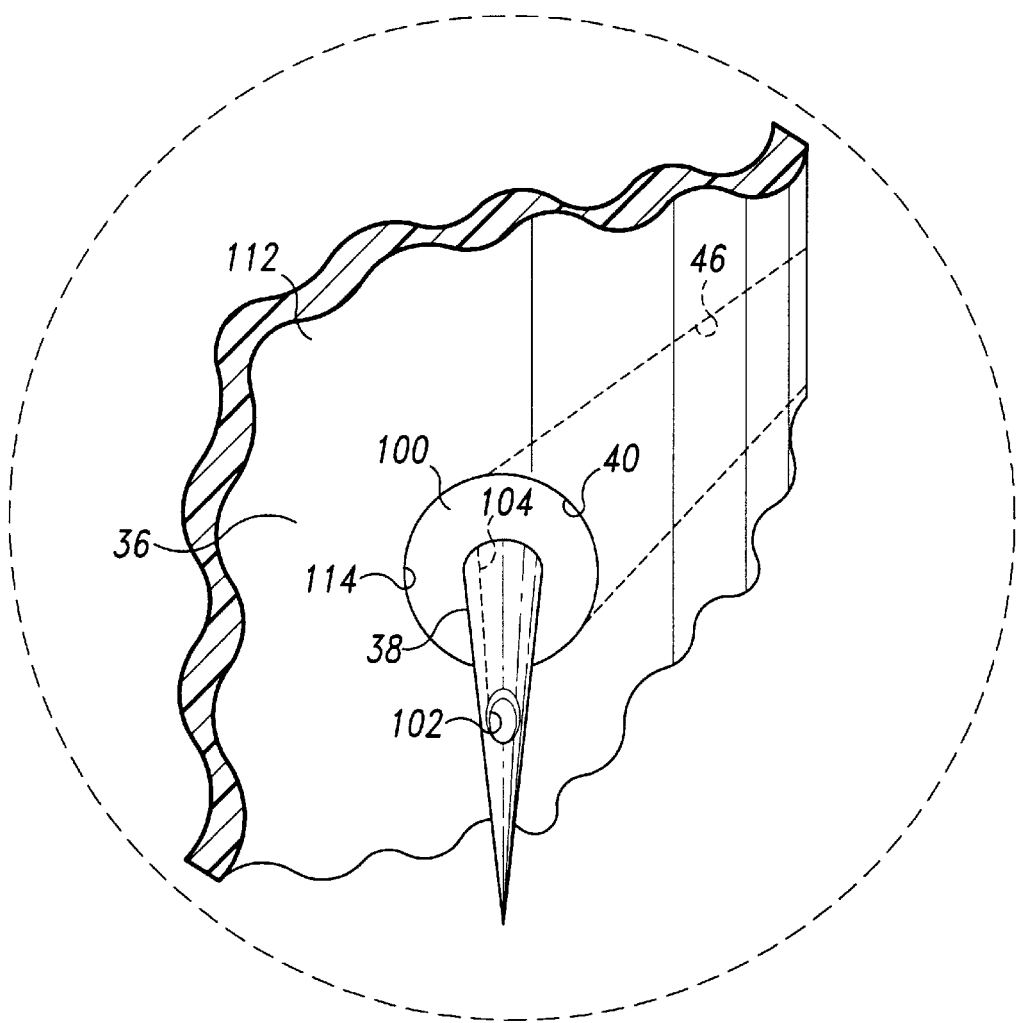
FIG. 8 is an enlarged view of a portion of FIG. 3 which is encircled and indicated as FIG. 8.

As shown in FIG. 8, housing 34 includes a fluid delivery needle 38 having a base 100 attached thereto which is positioned in contact with each entrance port end wall 40 of pressure line 46 such that each fluid delivery needle 38 extends into interior cavity 36 of housing 34 (see FIG. 3). Base 100 is secured to each entrance port end wall 40 with an appropriate adhesive (not shown). Each fluid delivery needle 38 has a needle aperture 102 defined therein. Needle aperture 102 leads to a lumen 104 which in turn leads to pressure line 46 thereby placing pressure line 46 in fluid communication with interior cavity 36 through fluid delivery needle 38.

Referring back to FIGS. 1–3, it should be understood that each fluid delivery channel 22 is preferably defined in wall 32 of cannula 16. Each fluid delivery channel 22 extends substantially along the entire length of cannula 16. In addition, each fluid delivery channel 22 has a number of exit ports 24 in fluid communication therewith which lead to outer surface 30 of cannula 16. As shown in FIG. 3, each fluid delivery channel 22 has a branched end 98 which extends into housing 34. Branched end 98 of each fluid delivery channel 22 defines three additional entrance ports 114 in interior wall segment 112 which lead to interior cavity 36 of housing 34 (i.e. there are a total of six entrance ports 114 defined by the pair of fluid delivery channels 22 and two entrance ports defined by pressure line 46). Each entrance port 114 defines an entrance port end wall 40. It should be understood that having entrance ports 114 positioned in the above described manner places fluid delivery channels 22 in fluid communication with interior cavity 36 of housing 34. In a manner substantially identical as that described above in reference to FIG. 8, a fluid delivery needle 38 is attached to each entrance port end wall 40 via a base 100 so as to place each fluid delivery channel 22 in fluid communication with interior cavity 36 through fluid delivery needle 38 (see FIG. 3).

As shown in FIG. 6, a pressure source 48 is connected to insufflation valve 108 via hose 116. It should be understood that when insufflation valve 108 is located in an open position (see FIG. 6), a pressurized fluid such as $CO_2$ can be advanced from pressure source 48 through hose 116 and insufflation valve 108, and into working channel 20 of cannula 16. Once in working channel 20, the fluid is advanced into body cavity 56 to cause insufflation thereof. It should be understood that insufflation valve 108 can also be located in a closed position (not shown) so as to prevent fluid from being advanced from pressure source 48 to body cavity 56. In addition, it should be appreciated that insufflation valve 108 can be located in a desufflate position (not shown) so as to allow pressurized fluid contained within an insufflated body cavity 56 to escape. Specifically, placing insufflation valve 108 in the desufflate position allows the pressurized fluid contained within an insufflated body cavity 56 to be advanced from body cavity 56 to the surrounding environment through working channel 20, insufflation valve 108, and an escape port 118 attached to insufflation valve 108.

It should also be understood that insufflation valve 108 and pressure control valve 50 can be positioned such that pressure line 46 (see FIG. 2) is in fluid communication with pressure source 48 via a fluid path defined by hose 116, insufflation valve 108, bleed line 106 (see FIG. 2), and pressure control valve 50. Therefore, it should be appreciated that pressurized fluid can be advanced from pressure source 48 to the pair of fluid delivery needles 38 in fluid communication with pressure line 46 (see FIG. 2).

Figure 4:
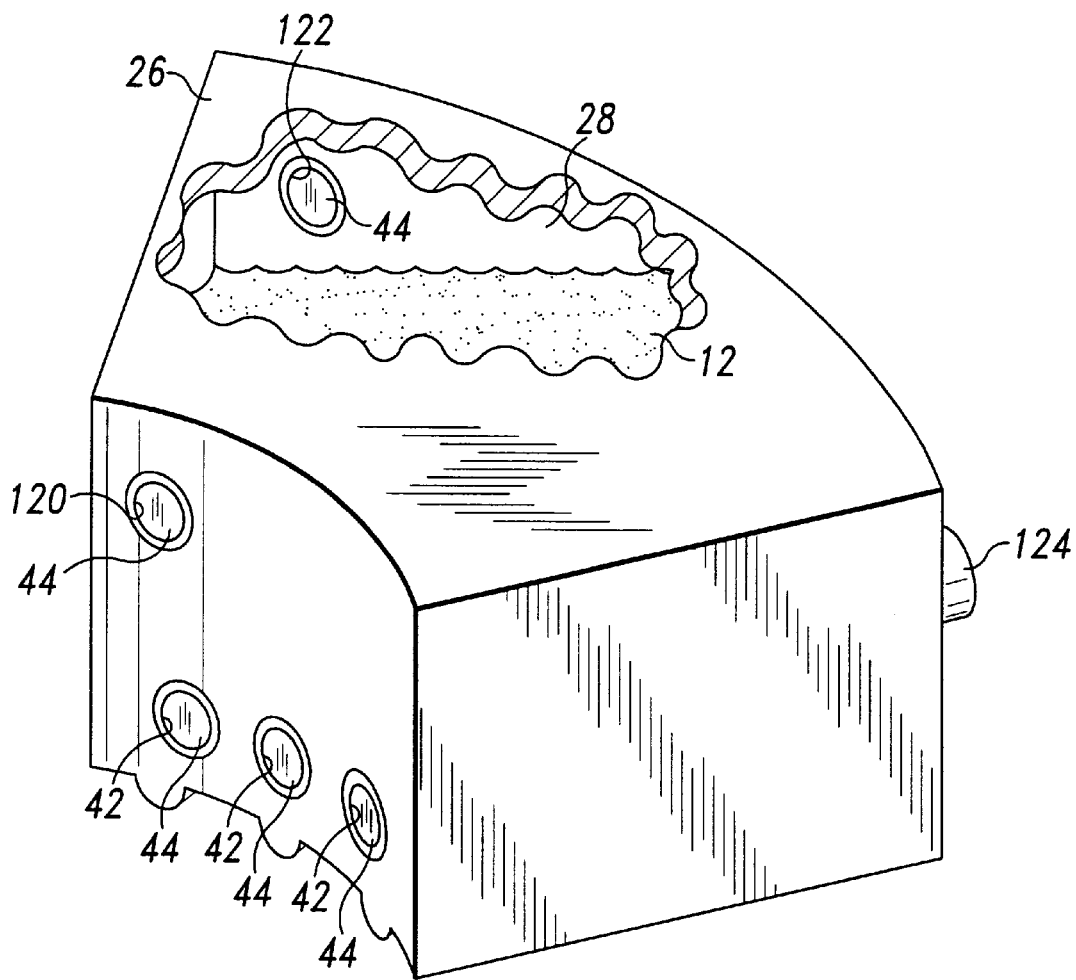
FIG. 4 is an enlarged perspective view of one of the chemical containers shown in FIG. 1.
Figure 5:
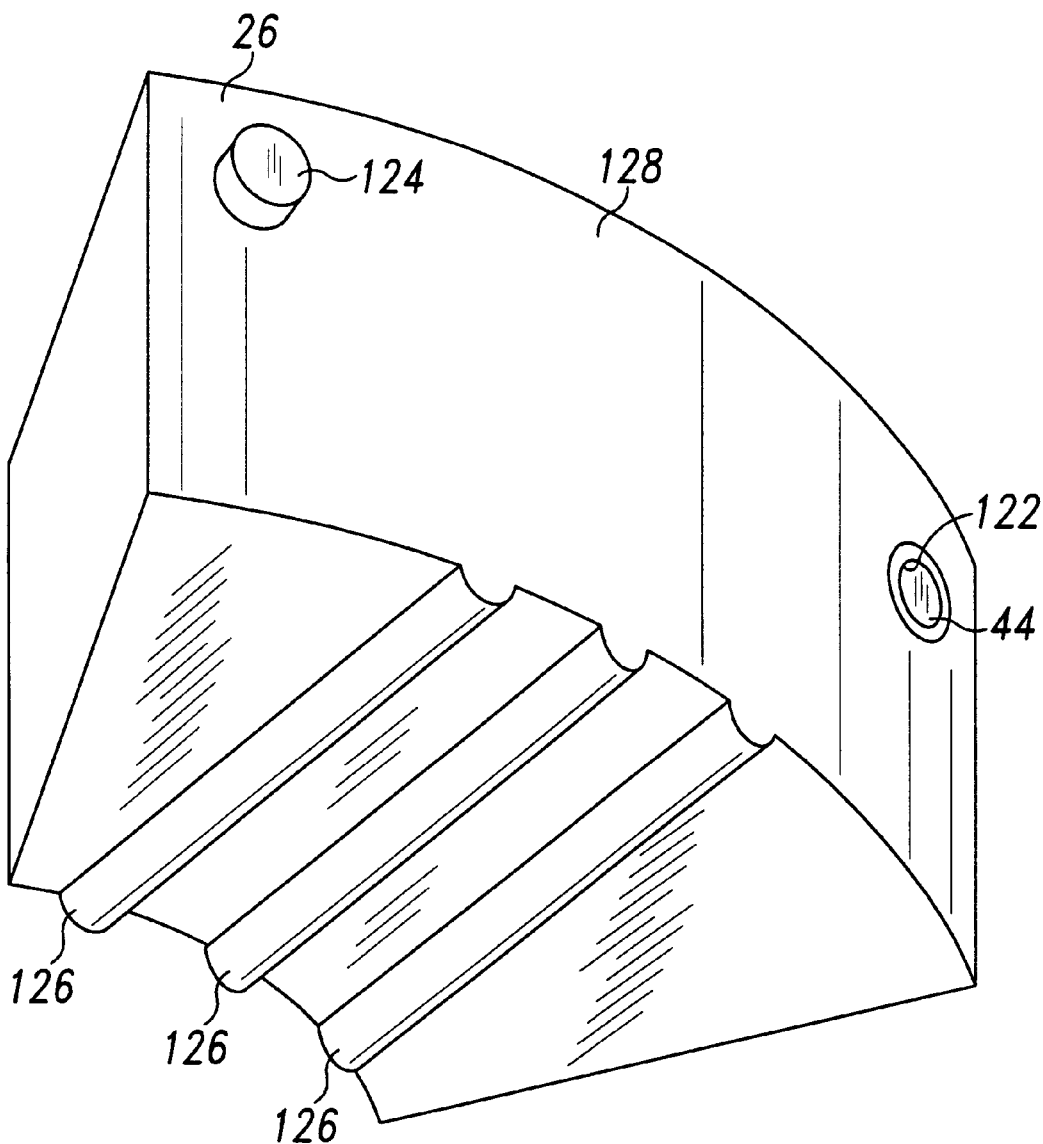
FIG. 5 is a view similar to FIG. 4, but showing an under portion of the chemical container.

Referring now to FIGS. 1, 2, 4, and 5, each chemical container 26 has an interior void 28 defined therein (see FIGS. 2 and 4) for receiving a biologically active compound 12. Each chemical container 26 also includes three exit apertures 42 defined therein (see FIG. 4) which are in fluid communication with interior void 28. Each exit aperture 42 has a diaphragm 44 positioned therein so as to prevent biologically active compound 12 from leaking out of interior void 28. Each diaphragm 44 can be made of, for example, silicone rubber. Each chemical container 26 also includes a pressure aperture 120 (see FIG. 4) in fluid communication with interior void 28. Each pressure aperture 120 has a diaphragm 44 positioned therein so as to form a fluid tight seal between interior void 28 and the exterior of chemical container 26. As shown in FIG. 5, each chemical container 26 further includes a loading aperture 122 with a diaphragm 44 positioned therein so as to prevent biologically active compound 12 from leaking out of interior void 28. Chemical containers 26 also include (1) a pressure relief valve 124 in fluid communication with interior void 28 and (2) three ribs 126 defined thereon.

Biologically active compound 12 includes chemical substances such as antibiotics, cytotoxic agents or compounds which effectively inhibit tumor cell adherence to a membrane. A large number of antimicrobial agents (i.e. antibiotics) or antiseptics are contemplated for use as biologically active compound 12 in the present invention. Preferably, where possible, the antibiotic should be active against both Gram-positive and Gram negative pathogens. The following are illustrative of the antibiotics and/or antiseptics which can be disposed in interior void 28 to aid in the control, inhibition, or prevention of infections of opening 52: (i) metal salts, or like compounds with antibacterial metal ions, e.g. copper or silver, and optionally with additional nonmetallic ions of antibacterial properties; (ii) topical antibiotics, e.g. neomycin, soframycin, bacitracin, polymcin; (iii) antibacterials such as chlorhexidine and its salts; (iv) quaternary ammonium compounds, e.g. centrimide, domiphen bromide, and polymeric quaternaries; (v) iodophors such as povidone iodine, and polyvinylpyrrolidone-iodine (PVP-I); (vi) acridine compounds such as 9-aminoacridine, 3,6-diaminoacridine and 6,9-diamino-2-ethoxyacridine; and (vii) biguanidine compounds such as 1,6-di(4-chlorophenylbiguanido)hexane, diaminohexylbiguanide, 1,6-di(aminohexylbiguanido) hexane, and polyhexamethylenebiguanide. Additional suitable antibiotics include aminoglycoside antibiotics such as amikacin, butirosin, dideoxykanamycin B (DKP), fortimycin, gentamycin, kanamycin, lividomycin, neomycin, netilmicin, ribostamycin, sagamycins, seldomycins and their epimers, sisomicin, sorbistin, tobramycin, streptomycins, linkomycins such as clindamycin, lincomycin and rifamycins such as rifampicin and rifamycin. Antibiotics such as polymyxin B sulfate-neomycin sulfate, cleocin phosphate® (available from the Upjohn Company, Kalamazoo, Mich.) and erythromycin ethylsuccinate are also contemplated.

Examples of suitable antiseptics include bromchlorophen, hexetidine, buclosamide, salicylic acid, cerium nitrate, chlorhexidine, 5-chloro-8-hydroxyquinoline, copper 8-hydroxyquinolate, acridine orange, undecenoic acid, undecoylium chloride and silver salts such as silver sulfadiazine, mafenide, nitrofurazole, cloflucarban, tribromasalan, taurolin and noxythiolin.

With respect to aiding in the control, inhibition or prevention of tumor cell adhesion and implantation and the subsequent metastasis via opening 52, compounds which effectively block or inhibit tumor cell adhesion (please note that tumor cell adhesion is a step in the metastasis cascade), or destroy tumor cells before adhering to a side wall 58 of opening 52, or other sites, can be disposed in interior void 28. Types of compounds which effectively block or inhibit tumor cell adherence include anticoagulants, fibrinolytic agents and compounds which alter the electrical charge of a membrane surface. For example, the surface charge altering and anticoagulant heparin can be disposed in interior void 28. Additionally, any of several water-soluble high molecular weight glucose polymers (average molecular weight (MW) 75 kdal) otherwise known as dextrans, can also be disposed in interior void 28 to alter the surface electrical charge of any contacted membranes thereby blocking tumor cell adhesion. Preferably a dextran having an average MW of about 40 kdal is used to coat outer surface 30.

As stated above, tumor cell destroying compounds, hereinafter referred to as cytotoxic compounds, can also be disposed in interior void 28. These compounds include cisplatin, carboplatin, 5-fluorouracil, providoneiodine, tumor necrosis factor (TNF)-$\alpha$, tauromustine, mitomycin C, camptothecin, bleomycin, indomethacin, N-methyl formamide, tamoxifen, sodiumhypochlorite, chlorhexidinecetrimide, adriamycin, methotrexate. Tumor cell destroying compounds also include antimetabolites such as cytarabine, azaribine, mercaptopurine, thioguanine; natural products such as vinblastine, vincristine, dactinomycin, daunorubicin, doxorubicin, bleomycin, mithramycin, mitomycin; and other miscellaneous agents such as cisplatin, hydroxyurea, procarbazine and mitotane, Alkylating agents such as mechlorethamine, nitrogen mustards, ethlenimine derivatives, alkyl sulfonates, nitrosoureas, and triazenes are also contemplated. Moreover, the compounds disclosed by Krakoff, Irwin H. in *Systemic Treatment of Cancer,* CA Cancer J. Clin., vol. 46, No. 3, pages 134–141 (May/June 1996), which is incorporated herein by reference, are contemplated for being disposed in interior void 28.

In addition antiangiogenesis agents such as angiostatin and endostatin are included in the group of cytotoxic compounds to be disposed in interior void 28. Moreover, antibodies, including human monoclonal antibodies are included as cytotoxic compounds. Preferably, the human monoclonal antibody HuMab SK1 as described by Chang, Helena R. et al. in *Human Monoclonal Antibody SK1-Mediated Cytotoxicity Against Colon Cancer Cells*, Dis. Colon Rectum, vol. 36, No. 12, pages 1152–1157 (December 1993) which is incorporated herein by reference, is disposed in interior void 28. Other monoclonal antibodies can also be disposed in interior void 28, for example those produced from hybridomas having the accession numbers HB8573, HB8232 and HB8250 available from the American Type Culture Collection, located at 12301 Parklawn Drive, Rockville Md., 20852. Furthermore, interleukin 2 (IL-2), cytokines or lymphokines are also included in the group of cytotoxic compounds of the present invention. Also contemplated are hyaluronate coating solutions. In addition, gene based cancer drugs are contemplated. Examples of such include gene based cancer drugs directed toward the RAS gene. Another example of a gene based cancer drug is a drug directed toward the EGF receptor (i.e. EGFR). It should also be understood that a combination of any of the above compounds can be disposed in interior void 28.

During use of medical apparatus 10, trocar 18 is initially located in a first trocar position as shown in phantom in FIG. 1 (i.e. trocar 18 is positioned within working channel 20 of cannula 16). In addition, chemical containers 26 are located outside of interior cavity 36 of housing 34 and doors 94 (see FIG. 3) are located in the closed position (not shown). Trocar 18 of medical apparatus 10 is then placed in contact with, and advanced through, wall 54 of body cavity 56 to create opening 52 as shown in FIG. 1. Once medical apparatus 10 is positioned as described above, trocar 18 is moved to a second trocar position (i.e. trocar 18 is completely removed from working channel 20 of cannula 16). Insufflation valve 108 is then located in the open position (see FIG. 6) so that pressurized $CO_2$ is advanced from pressure source 48 through hose 116 and insufflation valve 108, and into working channel 20 of cannula 16. Once in working channel 20, the pressurized $CO_2$ is advanced into body cavity 56 to cause insufflation thereof. Once body cavity 56 is insufflated a camera (not shown) is inserted down through working channel 20 and into body cavity 56 such that a surgeon can visually inspect the interior of body cavity 56 for possible signs of cancer (e.g. the presence of a tumor in body cavity 56) or an infection. If no signs of cancer or infection are detected, and the surgeon is satisfied that no cancer or infection is present within body cavity 56, the surgical procedure can proceed in a manner that is well known in the art.

However, if cancer or infection is detected within body cavity 56, or if the surgeon suspects cancer or an infection is present, each chemical container 26 is loaded with a predetermined amount of an appropriate biologically active compound 12. Specifically, a syringe (not shown) is filled with a predetermined amount of the appropriate biologically active compound 12 and the hypodermic needle of the syringe is inserted through diaphragm 44 of loading aperture 122 (see FIG. 5). The predetermined amount of biologically active compound 12 is then advanced from the syringe through the hypodermic needle and into interior void 28 (see FIG. 4) of chemical container 26 in a well known manner. Once an appropriate amount of biologically active compound 12 has been disposed within interior void 28 the hypodermic needle of the syringe is withdrawn from diaphragm 44 of loading aperture 122. It should be understood that diaphragm 44 will self seal once the hypodermic needle is removed therefrom to prevent any biologically active compound 12 from leaking out through loading aperture 122. It should also be understood that having a posterior wall 128 (see FIG. 5) of chemical container 26 made from a transparent or translucent substance (e.g. plastic) is contemplated so that the surgeon can visually confirm that the chemical container 26 is loaded with biologically active compound 12.

Once both chemical containers 26 are loaded in the above described manner, each door 94 (see FIG. 3) is located in the open position and each chemical container 26 is positioned within housing 34 of cannula 16. Specifically, as shown in FIG. 1, each chemical container 26 is positioned relative to housing 34 such that exit apertures 42 and pressure aperture 120 face passageways 88. Each chemical container 26 is further positioned relative to housing 34 such that ribs 126 (see FIG. 5) formed on chemical container 26 are aligned with corresponding grooves 130 (see FIG. 3) defined in exterior wall segment 110. Both chemical containers 26 are then advanced toward passageways 88 such that ribs 126 are positioned within grooves 130 and both chemical containers 26 are partially located within interior cavity 36 of housing 34.

It should be understood that positioning ribs 126 within grooves 130 in the above described manner aligns each fluid delivery needle 38 in fluid communication with fluid delivery channel 22 (see FIG. 3) with a corresponding diaphragm 44 positioned within an exit aperture 42 (see FIG. 4). In addition, positioning ribs 126 within grooves 130 aligns each fluid delivery needle 38 in fluid communication with pressure line 46 (see FIG. 3) with a corresponding diaphragm 44 positioned within a pressure aperture 120 (see FIG. 4). Once aligned in the above described manner, both chemical containers 26 are advanced further into interior cavity 36 until each fluid delivery needle 38 in fluid communication with a fluid delivery channel 22 pierces and is advanced through the corresponding diaphragm 44 positioned within an exit aperture 42 (see FIG. 2). In a similar manner, both fluid delivery needles 38 in fluid communication with pressure line 46 pierce and are advanced through the corresponding diaphragm 44 positioned within pressure aperture 120 (see FIG. 2). Advancing fluid delivery needles 38 through diaphragms 44 in the above described manner places each fluid delivery channel 22 in fluid communication with interior void 28 of the corresponding chemical container 26. In addition, pressure line 46 is placed in fluid communication with interior void 28 of each chemical container 26.

After placing fluid delivery channels 22 and pressure line 46 in fluid communication with interior void 28 of each chemical container 26 doors 94 are located in the closed position. Insufflation valve 108 and pressure control valve 50 are then positioned such that pressure line 46 (see FIG. 2) is in fluid communication with pressure source 48. Pressurized fluid (i.e. $CO_2$) is then advanced from pressure source 48 into interior void 28 of each chemical container 26 via the fluid delivery needles 38 extending through pressure apertures 120. Advancing fluid into interior void 28 increases the pressure therein. However, it should be understood that pressure control valve 50 can be adjusted to control the pressure within interior void 28 of each chemical container 26. It should also be understood that pressure relief valve 124 is designed to release an amount of the pressurized fluid if the pressure within interior void 28 becomes to great. Since interior void 28 of each chemical container 26 is in fluid communication with body cavity 56 via a fluid path defined by exit ports 24, fluid delivery channels 22, and fluid delivery needles 38, having pressure relief valve 124 designed in the above described manner also ensures that the pressure within body cavity 56 does not become to great.

Once biologically active compound 12 is located in fluid delivery channel 22, biologically active compound 12 is advanced along the length of cannula 16 in a direction indicated by arrow 132 as shown in FIG. 2. While being advanced in the above described manner, biologically active compound 12 comes into fluid communication with exit ports 24 (see FIG. 2). As biologically active compound 12 encounters each exit port 24 a portion of biologically compound 12 advances through each exit port 24 and is delivered to outer surface 30 of cannula 16 as shown in FIG. 1. The above described process of delivering biologically active compound 12 to outer surface 30 can be continued until both chemical containers 26 are substantially emptied and essentially all of biologically active compound 12 has been delivered to outer surface 30 of cannula 16. However, if required, the surgeon can reopen doors 94 and inject an additional predetermined amount of biologically compound 12 into each interior void 28 of chemical containers 26 as described above so as to continue the process of delivering biologically active compound 12 to outer surface 30.

It should be appreciated that as biologically active compound 12 is delivered to outer surface 30 of cannula 16 an amount of biologically active compound 12 is transferred from outer surface 30 to side wall 58 of opening 52 as shown in FIG. 1. In addition it should be appreciated that as biologically active compound 12 is delivered to outer surface 30 of cannula 16 an amount of biologically active compound 12 can be transferred from outer surface 30 to an inside surface 57 of body cavity 56 (see FIG. 1) by positioning cannula 16 at an angle relative to side wall 58. It should further be appreciated that biologically active compound 12 can be continuously transferred to side wall 58 and inside surface 57 such that essentially the entire amount of biologically active compound 12 contained in chemical containers 26 is transferred to side wall 58 and inside surface 57. Once located in contact with side wall 58 or inside surface 57, biologically active compound 12 establishes a "pharmacological barrier" that helps prevent tumor cell implantation in opening 52 and/or the contamination of opening 52 with viable infectious microbes. Therefore, once opening 52 is protected in the above described manner the surgical procedure can proceed.

If necessary, in order to keep biologically active compound 12 from falling or sliding off outer surface 30 due to gravity, or being advanced out of exit ports 24 to quickly, biologically active compound 12 can contain a suitable pharmaceutically acceptable carrier. Such pharmaceutically acceptable carriers include known excipients and auxiliaries which facilitate the processing of biologically active compound 12 into a preparation which has the appropriate consistency to be advanced out of exit ports 24 in a controlled manner and thus disposed on outer surface 30, side wall 58, and interior surface 57.

Suitable excipients which may be used to prepare a pharmaceutically acceptable carrier, such as a paste or a viscous solution, include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Additionally, silica, talc, stearic acid or salts thereof such as magnesium stearate or calcium stearate, and/or polyethylene glycol can be used.

In addition, a suspension of biologically active compound 12 may be disposed on outer surface 30 or side wall 58. Suitable vehicles for such suspensions include sesame oil or synthetic fatty acid esters, for example, ethyl oleate or triglycerides. Such suspensions can include substances which increase the viscosity of the suspension including, for example, sodium carboxymethyl cellulose, sorbitol and/or a dextran.

The exact formulation of a pharmaceutically acceptable carrier will depend upon the particular nature of biologically active compound 12 to be disposed upon outer surface 30 and is easily determinable by one of ordinary skill in the art from only routine experimentation.

Being able to deliver essentially all of biologically active compound 12 contained within chemical containers 26 to side wall 58 or into body cavity 56 allows a surgeon to accurately determine the total amount of biologically active compound 12 administered to a patient during a surgical procedure. Knowing the total amount of biologically active compound 12 administered to the patient allows the surgeon to accurately control the dose administered to the patient and thus ensure that a proper dosage regimen for that particular patient is followed. The proper dosage regimen for a particular patient is dependent upon several factors including the age, sex, weight, condition of the recipient, kind of concurrent treatment, if any, frequency of treatment and the nature of the effect desired. In addition, the dosage regimen will also depend upon the immunologic status of the patient and the aggressiveness of the tumor. Moreover, the amount of biologically active compound 12 administered to the patient should be large enough to produce the desired effect but not so large as to cause adverse side effects, such as unwanted cross reactions, impaired wound healing, bleeding, impaired platelet function, anaphylactic reactions and the like. Counterindication, if any, immune tolerance and other variables will also affect the proper amount administered to the patient. The exact formulation of a pharmaceutically acceptable carrier and the amount of biologically active compound 12 contained therein (and therefore the amount administered to the patient) is easily determinable by one of ordinary skill In the art from only routine experimentation and by applying well know principles of therapeutics as set forth, for example, in Gilman, Alfred G. et al., eds., *The Pharmacological Basis of Therapeutics*, $6^{th}$ Edition, Macmillan Publishing Co., Inc. New York, N.Y. (1980) which is herein incorporated by reference. Preferably, such preparations will contain about 0.001 to about 99 percent biologically active compound 12 together with the pharmaceutically acceptable carrier.

The above described ability of the present invention which allows a surgeon to accurately determine the total amount of biologically active compound 12 disposed on outer surface 30 (and thus administered to a patient) during a surgical procedure represents a significant advantage over other methods of disposing biologically active compound 12 onto a medical apparatus (e.g. dipping the medical apparatus in a solution or suspension of biologically active compound 12 or the unquantified irrigation of opening 52 with biologically active compound 12). Specifically, many of the less accurate methods do not allow the surgeon to accurately control the amount of biologically active compound 12 administered to the patient. Therefore, these less accurate methods of disposing biologically active compound 12 onto the medical apparatus make it very difficult for the surgeon to ensure that a proper dosage regimen for a particular patient or cancer is being followed.

The present invention also allows a surgeon to avoid utilizing a biologically active compound 12 until it is deemed necessary. This is not possible with the aforementioned less accurate methods. For example, the dipping of a medical apparatus (i.e. a medical apparatus similar to medical apparatus 10) in a solution or suspension of biologically active compound 12 must be performed prior to the beginning of the surgery at a time when the surgeon has not visually confirmed the presence of cancer or infection in body cavity 56. The surgeon must dispose biologically active compound 12 on the medical device before the beginning of the surgery since withdrawing the medical apparatus after the surgery has started would cause a loss of the insufflation of body cavity 56 which can complicate the surgical procedure. Therefore, in many circumstances the surgeon will unnecessarily utilize biologically active compound 12 when no cancer or an infection is present which increases the cost of the surgical procedure. This is in contrast to the present invention which allows the surgeon to (1) begin the surgical procedure, (2) confirm whether biologically active compound 12 is required, and (3) only if needed, administer an accurate controllable amount of biological compound 12 to the patient without interrupting the surgical procedure and withdrawing medical apparatus 10 from body cavity 56.

Second Embodiment of the Invention

Figure 7:
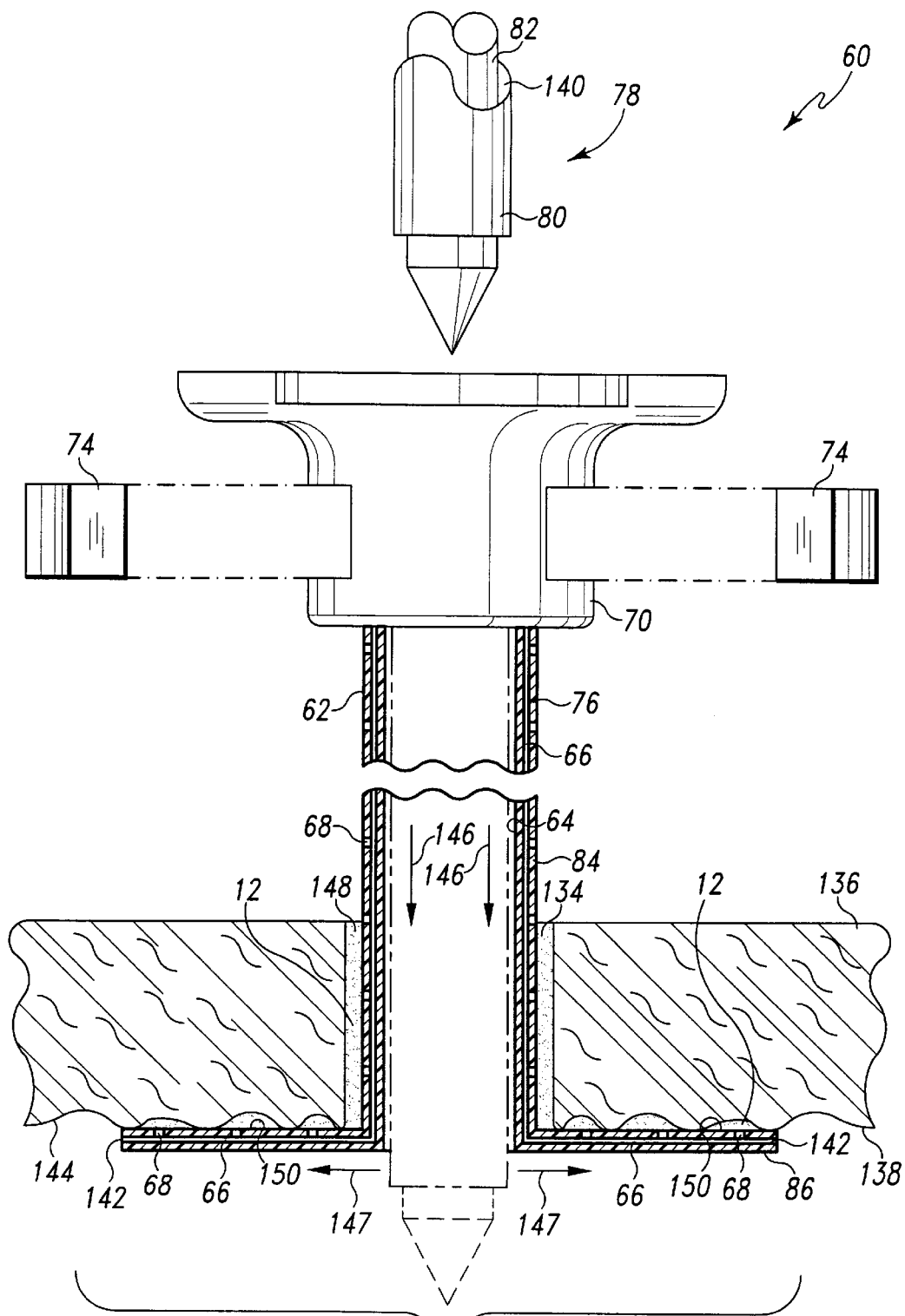
FIG. 7 is a cross sectional view of a second embodiment of the medical apparatus of the present invention.

Now referring to FIG. 7, there is shown a medical apparatus 60 similar to the medical apparatus 10 shown in FIG. 1. Medical apparatus 60 is shown advanced through an opening 134 in a wall 136 of a body cavity 138. Medical apparatus 60 includes a trocar assembly 78, a sleeve 62, and a pair of chemical containers 74. Trocar assembly 78 includes a trocar 82 positioned within a lumen 140 of a cannula 80. Trocar 82 is positionable between a first trocar position and a second trocar position as described above for trocar 18 (i.e. trocar 82 is positioned with lumen 140 of cannula 80 in the first trocar position and completely removed from lumen 140 in the second trocar position).

Sleeve 62 is substantially identical in construction to cannula 16 discussed above in reference to FIGS. 1, 2, 3, and 6 with the exception that sleeve 62 includes a sealing member 86 extending therefrom. For example, sleeve 62 also includes (1) a wall 84 having an outer surface 76, (2) a working channel 64 defined by wall 84, (3) a housing 70, and (4) a pair of fluid delivery channels 66 which are distinct from working channel 64 and are in fluid communication with a number of exit ports 68. As shown in FIG. 7, fluid delivery channels 66 are preferably defined in wall 84 of sleeve 62 and extend all the way to an end 142 of sealing member 86. It should be understood that sealing member 86 operates in a substantially identical manner, and has a substantially identical construction and function, as sealing members described in a U.S. patent application filed on Oct. 21, 1997 having application Ser. No. 08/955,256 (inventor Stephen P. Moenning) which is incorporated herein by reference, with the exception that sealing member 86 has fluid delivery channels 66 and exit ports 68 defined therein.

It should be understood that housing 70 is substantially identical in construction to housing 34 discussed above. Furthermore, fluid delivery channels 66 are in fluid communication with the interior cavity (not shown) of housing 70 in a substantially identical manner as described above in reference to fluid delivery channels 22.

Moreover, each chemical container 74 is constructed in a substantially identical manner as that described above for chemical containers 26. For example, each chemical container 74 has an interior void (not shown; see FIG. 3) defined therein for receiving biologically active compound 12.

Medical apparatus 60 is used in a similar fashion as that described above for medical apparatus 10 with some modifications to account for the presence of sleeve 62. Specifically, trocar 82 is initially located in the first trocar position, and trocar assembly 78 is positioned within working channel 64 of sleeve 62 as shown in phantom in FIG. 7. Sealing member 86 is then positioned in a substantially parallel relationship with working channel 64 of sleeve 62. Trocar 82 of medical apparatus 60 is then placed in contact with, and advanced through, wall 136 of body cavity 138 to create opening 134. Once medical apparatus 60 is positioned as described above, trocar 82 is moved to the second trocar position. Sealing member 86 is then positioned in a substantially orthogonal relationship with working channel 64 of sleeve 62 as shown in FIG. 7. Sleeve 62 is then positioned relative to opening 134 such that sealing member 86 makes contact with an interior surface 144 of body cavity 138.

Body cavity 138 is then insufflated in a similar manner as that described above in reference to FIG. 6 (i.e. body cavity 134 is insufflated via the insufflation valve (not shown) attached to housing 70 and pressure source 48. Once body cavity 138 is insufflated, and as previously discussed a determination is made that biologically active compound 12 is required based upon the presence of a cancer or an infection within body cavity 138, chemical containers 74 are loaded with biologically active compound 12 as previously described. Once loaded, chemical containers 74 are positioned within the interior cavity (not shown) of housing 70 in a substantially identical manner as that previously described above in reference to FIGS. 1–5. That is, chemical containers 74 are positioned within the interior cavity of housing 74 such that the interior void of each chemical container 74 is in fluid communication with (1) a fluid delivery channel 66 and (2) a pressure line defined in housing 70 which is substantially identical to pressure line 46 defined in housing 34 (see FIG. 2).

Once chemical containers 74 are positioned in the above described manner, the insufflation valve (not shown) and a pressure control valve (not shown) attached to housing 70 (i.e. a pressure control valve substantially identical to pressure control valve 50) are manipulated such that the interior void of each chemical container 74 is in fluid communication with pressure source 48. Bringing the interior void of each chemical container 74 into fluid communication with pressure source 48 advances biologically active compound 12 contained therein into each fluid delivery channel 66.

Once biologically active compound 12 is located in fluid delivery channel 66, biologically active compound 12 is advanced along the length of sleeve 62 and sealing member 86 in a direction indicated by arrows 146 and 147 as shown in FIG. 7. While being advanced in the above described manner, biologically active compound 12 comes into fluid communication with exit ports 68. As biologically active compound 12 encounters each exit port 68 a portion of biologically compound 12 advances through each exit port 68 and is delivered to outer surface 76 of sleeve 62 in a manner similar to that shown in FIG. 1. In addition, an amount of biologically active compound 12 is delivered to a contact surface 150 of sealing member 86. It should be appreciated that as biologically active compound 12 is delivered to outer surface 76 of sleeve 62 an amount of biologically active compound 12 is transferred from outer surface 76 to side wall 148 of opening 134 as shown in FIG. 7. In addition, it should be appreciated that as biologically active compound 12 is delivered to contact surface 150 of sealing member 86 an amount of biologically active compound 12 is transferred from contact surface 150 into contact with interior surface 144 of body cavity 138. It should further be appreciated that biologically active compound 12 can be continuously transferred to side wall 148 and interior surface 144 such that essentially the entire amount of biologically active compound 12 contained in chemical containers 74 is transferred to side wall 148 and interior surface 144. Once located in contact with side wall 148 and interior surface 144, biologically active compound 12 establishes a "pharmacological barrier" that helps prevent tumor cell implantation in opening 134 and/or the contamination of opening 134 with viable infectious microbes. Therefore, it should be understood that medical apparatus 60 has all of the advantages as described above in reference to medical apparatus 10.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected. For example, while chemical containers 26 and 74 are described above as being separate from housings 34 and 70, respectively, other arrangements are contemplated. One such arrangement incorporates chemical containers 26 and 74 into housings 34 and 70, respectively, such that each chemical container is "built in" or integral to the housing.

What is claimed is:

1. A medical apparatus for dispensing a biologically active compound, comprising:

a trocar assembly including a cannula and a trocar, wherein (1) said cannula has a working channel defined therein configured such that (i) said trocar is positionable therein and (ii) medical instruments may be advanced therethrough, (2) said cannula includes a fluid delivery channel which is distinct from said working channel, and (3) said fluid delivery channel has an exit port; and a chemical container having an interior void defined therein for receiving said biologically active compound, said interior void being in fluid communication with said exit port through said fluid delivery channel, wherein said biologically active compound may be delivered through said fluid delivery channel to an outer surface of said cannula through a fluid path defined by said fluid delivery channel and said exit port, wherein (i) said cannula includes a housing, (ii) said housing has an interior cavity defined therein, and (iii) said chemical container is positioned within said interior cavity of said housing.

2. The medical apparatus of claim 1 further comprising a fluid delivery needle, said fluid delivery channel defines an entrance port end wall, said fluid delivery needle is attached to said entrance port end wall such that said fluid delivery needle is in fluid communication with said fluid delivery channel, said chemical container has an exit aperture defined therein with a diaphragm positioned in said exit aperture, and said fluid delivery needle extends through said diaphragm when said chemical container is positioned within said housing so as to place said interior void of said chemical container in fluid communication with said fluid delivery channel.

3. A medical apparatus for dispensing a biologically active compound, comprising:

a trocar assembly including a cannula and a trocar, wherein (1) said cannula has a working channel defined therein configured such that (i) said trocar is positionable therein and (ii) medical instruments may be advanced therethrough, (2) said cannula includes a fluid delivery channel which is distinct from said working channel, and (3) said fluid delivery channel has an exit port;

a chemical container having an interior void defined therein for receiving said biologically active compound, said interior void being in fluid communication with said exit port through said fluid delivery channel, wherein said biologically active compound may be delivered through said fluid delivery channel to an outer surface of said cannula through a fluid path defined by said fluid delivery channel and said exit port, a pressure line; and a pressure source which is in fluid communication with said interior void of said chemical container through said pressure line such that fluid can be advanced from said pressure source to said interior void of said chemical container so as to increase pressure within said interior void.

4. The medical apparatus of claim 3, further comprising:

a pressure control valve positioned within said pressure line for controlling pressure within said interior void of said chemical container.

5. A medical procedure for dispensing a biologically active compound, comprising the steps of:

creating an opening in a wall of a body cavity;

advancing a medical apparatus through the opening and into the body cavity, said medical apparatus including a trocar assembly having (1) a cannula and a trocar, wherein (A) said cannula has a working channel defined therein configured such that (i) said trocar is positionable therein and (ii) medical instruments may be advanced therethrough, (B) said cannula includes a fluid delivery channel which is distinct from said working channel, and (C) said fluid delivery channel has an exit port, and (2) a chemical container having an interior void defined therein for receiving said biologically active compound, said interior void being in fluid communication with said exit port through said fluid delivery channel; and advancing said biologically active compound from said interior void of said chemical container onto an exterior surface of said cannula through a fluid path defined by said fluid delivery channel, wherein (i) said cannula includes a housing, (ii) said housing has an interior cavity defined therein, and (iii) said chemical container is positioned within said interior cavity of said housing.

6. The medical procedure of claim 5, wherein:

said medical apparatus further comprises a fluid delivery needle, said fluid delivery channel defines an entrance port end wall, said fluid delivery needle is attached to said entrance port end wall such that said fluid delivery needle is in fluid communication with said fluid delivery channel, said chemical container has an exit aperture defined therein with a diaphragm positioned in said exit aperture, and said fluid delivery needle extends through said diaphragm when said chemical container is positioned within said housing so as to place said interior void of said chemical container in fluid communication with said fluid delivery channel.

7. A medical procedure for dispensing a biologically active compound, comprising the steps of:

creating an opening in a wall of a body cavity;

advancing a medical apparatus through the opening and into the body cavity, said medical apparatus including a trocar assembly having (1) a cannula and a trocar, wherein (A) said cannula has a working channel defined therein configured such that (i) said trocar is positionable therein and (ii) medical instruments may be advanced therethrough, (B) said cannula includes a fluid delivery channel which is distinct from said working channel, and (C) said fluid delivery channel has an exit port, and (2) a chemical container having an interior void defined therein for receiving said biologically active compound, said interior void being in fluid communication with said exit port through said fluid delivery channel; and advancing said biologically active compound from said interior void of said chemical container onto an exterior surface of said cannula through a fluid path defined by said fluid delivery channel wherein said medical apparatus further includes a pressure line, a pressure source which is in fluid communication with said interior void of said chemical container through said pressure line such that fluid can be advanced from said pressure source to said interior void of said chemical container so as to increase pressure within said interior void, and said biologically active compound advancing step includes the step of increasing pressure within said interior void of said chemical container by advancing fluid from said pressure source through said pressure line and into said interior void of said chemical container.

8. The medical procedure of claim 7, wherein:

said medical apparatus further includes a pressure control valve positioned within said pressure line for controlling pressure within said interior void of said chemical container.

9. A medical apparatus for dispensing a biologically active compound, comprising:

a sleeve, wherein (1) said sleeve has a working channel defined therein through which medical instruments may be advanced, (2) said sleeve includes a fluid delivery channel which is distinct from said working channel, (3) said fluid delivery channel has an exit port, and (4) said sleeve includes a housing having an interior cavity defined therein;

a chemical container having an interior void defined therein for receiving said biologically active compound, wherein said interior void is in fluid communication with said exit port through said fluid delivery channel when said chemical container is positioned within said interior cavity of said housing such that said biologically active compound may be delivered through said fluid delivery channel to an outer surface of said sleeve; and a fluid delivery needle, wherein (i) said fluid delivery channel defines an entrance port end wall, (ii) said fluid delivery needle is attached to said entrance port end wall such that said fluid delivery needle is in fluid communication with said fluid delivery channel, (iii) said chemical container has an exit aperture defined therein with a diaphragm positioned in said exit aperture, and (iii) said fluid delivery needle extends through said diaphragm when said chemical container is positioned within said housing so as to place said interior void of said chemical container in fluid communication with said fluid delivery channel.

10. A medical apparatus for dispensing a biologically active compound, comprising:

a sleeve, wherein (1) said sleeve has a working channel defined therein through which medical instruments may be advanced, (2) said sleeve includes a fluid delivery channel which is distinct from said working channel, (3) said fluid delivery channel has an exit port, and (4) said sleeve includes a housing having an interior cavity defined therein;

a chemical container having an interior void defined therein for receiving said biologically active compound, wherein said interior void is in fluid communication with said exit port through said fluid delivery channel when said chemical container is positioned within said interior cavity of said housing such that said biologically active compound may be delivered through said fluid delivery channel to an outer surface of said sleeve;

a pressure line; and a pressure source which is in fluid communication with said interior void of said chemical container through said pressure line such that fluid can be advanced from said pressure source to said interior void of said chemical container so as to increase pressure within said interior void.

* * * * *